(12) United States Patent
Shim et al.

(10) Patent No.: US 10,585,035 B2
(45) Date of Patent: Mar. 10, 2020

(54) SPECTROMETER, METHOD OF CONTROLLING OUTPUT GAIN OF SPECTROMETER, AND APPARATUS AND METHOD FOR MEASURING BIO-INFORMATION

(71) Applicant: SAMSUNG ELECTRONICS CO., LTD., Suwon-si (KR)

(72) Inventors: Jae Wook Shim, Yongin-si (KR); Hyo Sun Hwang, Seoul (KR); Hyun Seok Moon, Seoul (KR); Hyeong Seok Jang, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/928,247

(22) Filed: Mar. 22, 2018

(65) Prior Publication Data

US 2019/0154568 A1 May 23, 2019

(30) Foreign Application Priority Data

Nov. 22, 2017 (KR) .................... 10-2017-0156785

(51) Int. Cl.
  *G01N 21/31* (2006.01)
  *H03G 3/30* (2006.01)
  *G01N 33/49* (2006.01)
  *G01J 3/28* (2006.01)
  *G01J 3/02* (2006.01)
  (Continued)

(52) U.S. Cl.
  CPC ............ *G01N 21/31* (2013.01); *G01J 3/0264* (2013.01); *G01J 3/0272* (2013.01); *G01J 3/10* (2013.01); *G01J 3/28* (2013.01); *G01J 3/32* (2013.01); *G01J 3/42* (2013.01); *G01N 21/255* (2013.01); *G01N 33/49* (2013.01); *H03G 3/3084* (2013.01); *G01N 2201/0221* (2013.01)

(58) Field of Classification Search
  None
  See application file for complete search history.

(56) References Cited

U.S. PATENT DOCUMENTS 5,365,066 A * 11/1994 Krueger, Jr. ....... A61B 5/02433
                                                                          250/339.12
6,345,765 B1    2/2002 Wiklof
                        (Continued)

FOREIGN PATENT DOCUMENTS

JP       8-101121 A     4/1996
JP   2000-314662 A    11/2000
                        (Continued)

OTHER PUBLICATIONS

Communication dated Jan. 9, 2019, issued by the European Patent Office in counterpart European Application No. 18180746.2.

*Primary Examiner* — Shawn Decenzo
(74) *Attorney, Agent, or Firm* — Sughrue Mion, PLLC

(57) ABSTRACT

Provided is a spectrometer. The spectrometer includes: a light source part configured to emit light of a plurality of wavelengths onto an object; a detector configured to detect an optical signal of each of the plurality of wavelengths as reflected from the object; a controller configured to set an amplification gain for each of the plurality of wavelengths according to photoreaction properties of the object; and an amplifier configured to amplify an output signal of the detector by using the set amplification gain.

15 Claims, 15 Drawing Sheets

US 10,585,035 B2
Page 2

(51) Int. Cl.
    *G01J 3/10*     (2006.01)
    *G01J 3/42*     (2006.01)
    *G01J 3/32*     (2006.01)
    *G01N 21/25*     (2006.01)

(56) References Cited

U.S. PATENT DOCUMENTS

| | | | |
|---|---|---|---|
| 6,716,300 B2 | 4/2004 | Kaji et al. | |
| 7,445,790 B2 | 11/2008 | Oguchi et al. | |
| 7,489,398 B2 | 2/2009 | Otoi | |
| 8,633,841 B2 * | 1/2014 | Oonishi | H01J 49/025 |
| | | | 341/139 |
| 9,250,132 B2 * | 2/2016 | Bonyuet | G01J 3/02 |
| 2005/0154268 A1 * | 7/2005 | Hwang | A61B 5/14532 |
| | | | 600/316 |
| 2010/0148083 A1 * | 6/2010 | Brown | G01J 3/02 |
| | | | 250/372 |
| 2012/0212744 A1 * | 8/2012 | Okada | G01N 21/39 |
| | | | 356/437 |
| 2016/0149378 A1 * | 5/2016 | Kinoshita | H01S 5/06817 |
| | | | 359/337 |
| 2016/0259432 A1 * | 9/2016 | Bau | H04W 4/023 |
| 2017/0007097 A1 * | 1/2017 | Takei | A61B 1/04 |
| 2017/0126190 A1 * | 5/2017 | Nakhkoob | H03G 3/3084 |
| 2017/0370828 A1 * | 12/2017 | Arifin | G01N 21/31 |
| 2018/0180533 A1 * | 6/2018 | Murakami | G01N 21/27 |
| 2018/0183517 A1 * | 6/2018 | Sugiyama | H04B 10/07957 |
| 2018/0188129 A1 * | 7/2018 | Choudhury | G01M 3/04 |
| 2018/0209845 A1 * | 7/2018 | Huang | G01J 1/44 |
| 2019/0033217 A1 * | 1/2019 | Kim | G01N 21/65 |
| 2019/0154656 A1 * | 5/2019 | Bae | G01N 21/3103 |
| 2019/0257759 A1 * | 8/2019 | Han | G01N 21/314 |

FOREIGN PATENT DOCUMENTS

| | | |
|---|---|---|
| JP | 3461982 B2 | 10/2003 |
| JP | 2010-73863 A | 4/2010 |
| JP | 2015-64228 A | 4/2015 |
| JP | 5899866 B2 | 4/2016 |
| KR | 10-2008-0083090 A | 9/2008 |

\* cited by examiner

SPECTROMETER, METHOD OF CONTROLLING OUTPUT GAIN OF SPECTROMETER, AND APPARATUS AND METHOD FOR MEASURING BIO-INFORMATION

CROSS-REFERENCE TO RELATED APPLICATION(S)

This application claims priority from Korean Patent Application No. 10-2017-0156785, filed on Nov. 22, 2017, in the Korean Intellectual Property Office, the entire disclosure of which is incorporated herein by reference for all purposes.

BACKGROUND

1. Field

Apparatuses and methods consistent with exemplary embodiments relate to a spectrometer, and technology for measuring bio-information using the spectrometer, and more particularly to technology for adjusting an output gain of a light receiving stage of the spectrometer.

2. Description of the Related Art

Recently, research has been conducted on methods of measuring bio-information, such as blood glucose, in a non-invasive manner using Raman spectroscopy or a near-infrared spectrometer. In such bio-information measuring methods, a spectrum of light reflected from an object is measured using a spectrometer, and bio-information including blood glucose, calories, and the like is determined based on the measured spectrum. Generally, the spectrometer includes a light source which emits light onto the object, such as portion of the human body, and a detector which detects an optical signal returning from the object. A current signal detected by the detector is converted into a voltage signal and is amplified by the amplifier, and an output signal of the amplifier is converted into a digital signal and is output by an Analog Digital Converter (ADC).

SUMMARY

According to an aspect of an exemplary embodiment, there is provided a spectrometer including: a light source part configured to emit light of a plurality of wavelengths onto an object; a detector configured to detect an optical signal of each of the plurality of wavelengths reflected by returning from the object according to the emitted light; a controller configured to set an amplification gain for each of the plurality of wavelengths according to photoreaction properties of the object; and an amplifier configured to amplify an output signal of the detector by using the set amplification gain.

The light source part may include a plurality of light sources, among which at least two of the plurality of light sources may emit light of different wavelengths.

The light source part may time-divide light of each of the plurality of wavelengths.

The controller may calculate an optimal amplification gain for each of the wavelengths based on the photoreaction properties of the object for each of the wavelengths, and when light of a specific wavelength is emitted by the light source part, the controller may set an amplification gain of the amplifier based on an optimal amplification gain of the specific wavelength.

The controller may calculate an optimal amplification gain, which does not saturate an output of the amplifier, for each of the plurality of wavelengths by changing an amplification gain of the amplifier in a predetermined amplification gain section.

The amplifier may include: a Trans-Impedance Amplifier (TIA) configured to convert a current signal output by the detector into a voltage signal; and a Variable Gain Amplifier (VGA) configured to amplify the voltage signal by using the set amplification gain for each of the plurality of wavelengths.

The spectrometer may further include a converter configured to convert an analog signal for each of the plurality of wavelengths, which is amplified and output by the amplifier, into a digital signal.

The controller may reconstruct a spectrum based on the digital signal output by the converter for each of the plurality of wavelengths.

The controller may obtain a first spectrum response based on the digital signal of the converter for each of the plurality of wavelengths, may obtain a second spectrum response based on a value obtained by dividing the obtained first spectrum response by a value obtained by multiplying a light intensity and an optimal amplification gain for each of the plurality of wavelengths, and may reconstruct a spectrum for measuring bio-information based on the obtained second spectrum response.

According to an aspect of another exemplary embodiment, there is provided a method of obtaining a spectrum by a spectrometer, the method including: emitting light of a plurality of wavelengths onto an object by a light source part; setting an amplification gain for each of the plurality of wavelengths according to photoreaction properties of the object by a controller; detecting, by a detector, an optical signal of each of the plurality of wavelengths as reflected from the object; and amplifying, by an amplifier, an output signal of the detector by using the set amplification gain.

Further, the spectrum obtaining method by the spectrometer may further include converting, by a converter, an analog signal, which is amplified and output by the amplifier for each of the plurality of wavelengths, into a digital signal.

In addition, the spectrum obtaining method by the spectrometer may further include reconstructing a spectrum based on the output digital signal for each of the plurality of wavelengths by the controller.

Moreover, the spectrum obtaining method by the spectrometer may further include: calculating, by the controller, an optimal amplification gain for each of the wavelengths based on the photoreaction properties of the object for each of the wavelengths; and setting of the amplification gain may include, when light of a specific wavelength is emitted in the emitting of the light onto the object, setting an amplification gain of the amplifier based on an optimal amplification gain of the specific wavelength.

The calculating of the optimal amplification gain may include: driving the light source part to emit light of a specific wavelength with a predetermined light intensity onto the object; while light of the specific wavelength is emitted onto the object, changing an amplification gain of the amplifier in a predetermined amplification gain section; and among the changed amplification gains, determining a maximum amplification gain, which does not saturate an output of the amplifier, to be an optimal amplification gain for the specific wavelength.

The determining of the optimal amplification gain may include, in response to the determined optimal amplification gain being equal to the maximum amplification gain in the amplification gain section, adjusting a light intensity of the wavelength, and repeating the emitting of the light and following operations.

According to an aspect of another exemplary embodiment, there is provided a bio-information measuring apparatus, including: an optical part including a light source part configured to emit light of a plurality of wavelengths onto an object, a detector configured to detect an optical signal as reflected from the object, and an amplifier configured to amplify an output signal of the detector by using an amplification gain set for each of the plurality of wavelengths; and a controller including a driving controller configured to control the light source part in response to a request for measuring bio-information, a gain controller, which when the light source part emits light of a specific wavelength, is configured to set an amplification of the amplifier based on an optimal amplification gain of the emitted specific wavelength, and a signal processor configured to measure bio-information based on the output signal of the optical part.

Upon receiving the request for measuring bio-information, the signal processor may determine whether to calculate an optimal amplification gain for each of the plurality of wavelengths for the object based on at least one of information about the object and sensor information.

In this case, the information about the object may include one or more of a gender of a user, an age of the user, a health state of the user, and a portion of the user to be examined that is contacted by the optical part; and the sensor information may include information collected from one or more of a tilt sensor and a contact pressure sensor.

Upon determining to calculate the optimal amplification gain by the signal processor, the driving controller may drive the light source part to emit light of each of the plurality of wavelengths with a predetermined light intensity; while the light source part emits light of each of the plurality of wavelengths, the gain controller may change the amplification gain of the amplifier in a predetermined amplification gain section; and the signal processor may determine a maximum amplification gain, which does not saturate an output of the amplifier, to be an optimal amplification gain for each of the plurality of wavelengths among the changed amplification gains.

In response to the determined optimal amplification gain being equal to the maximum amplification gain in the amplification gain section, the signal processor may adjust a light intensity and may re-calculate an optimal amplification gain with the adjusted light intensity.

The optical part may further include a converter configured to convert an analog signal for each of the plurality of wavelengths, which is amplified and output by the amplifier, into a digital signal; and the signal processor may reconstruct a spectrum based on the digital signal output by the converter for each of the plurality of wavelengths, and may measure bio-information by using the reconstructed spectrum.

The bio-information may include at least one of blood glucose, cholesterol, triglyceride, protein, and uric acid.

Further, the bio-information measuring apparatus may further include an output part configured to output a processing result of the controller.

According to an aspect of another exemplary embodiment, there is provided a bio-information measuring method, including: emitting light of a plurality of wavelengths onto an object by an optical part; when light of a specific wavelength is emitted, setting, by a controller, an amplification gain of a Variable Gain Amplifier (VGA) based on an optimal amplification gain of the emitted specific wavelength; by the optical part, detecting an optical signal of each of the plurality of wavelengths which is reflected from the object, and outputting an electric signal; amplifying the output electric signal by the optical part; and measuring bio-information based on the amplified and output signal by the controller.

In addition, the bio-information measuring method may further include: upon receiving the request for measuring bio-information, determining by the controller whether to calculate an optimal amplification gain for each of the plurality of wavelengths for the object; and upon determining to calculate the optimal amplification gain, calculating, by the controller, the optimal amplification gain for each of the plurality of wavelengths for the object.

The calculating of the optimal amplification gain may include: driving the light source part to emit light of a specific wavelength with a predetermined light intensity; while light of the specific wavelength is emitted onto the object, changing an amplification gain of the VGA in a predetermined amplification gain section; and among the changed amplification gains, determining a maximum amplification gain, which does not saturate an output signal of the VGA, to be an optimal amplification gain.

Further, the bio-information measuring method may further include: determining whether the determined optimal amplification gain is equal to the maximum amplification gain in the amplification gain section; and upon determination, in response to the determined optimal amplification gain being equal to the maximum amplification gain in the amplification gain section, adjusting a light intensity of a light source and proceeding to the driving of the light source.

In addition, the bio-information measuring method may further include: converting an analog signal for each of the plurality of wavelengths, which is amplified in the amplifying, into a digital signal.

The measuring of the bio-information may include: reconstructing a spectrum based on the digital signal for each of the plurality of wavelengths, and measuring the bio-information based on the reconstructed spectrum.

BRIEF DESCRIPTION OF THE DRAWINGS

These and/or other exemplary aspects and advantages will become apparent and more readily appreciated from the description, taken in conjunction with the accompanying drawings, in which.

DETAILED DESCRIPTION

Figure 1:
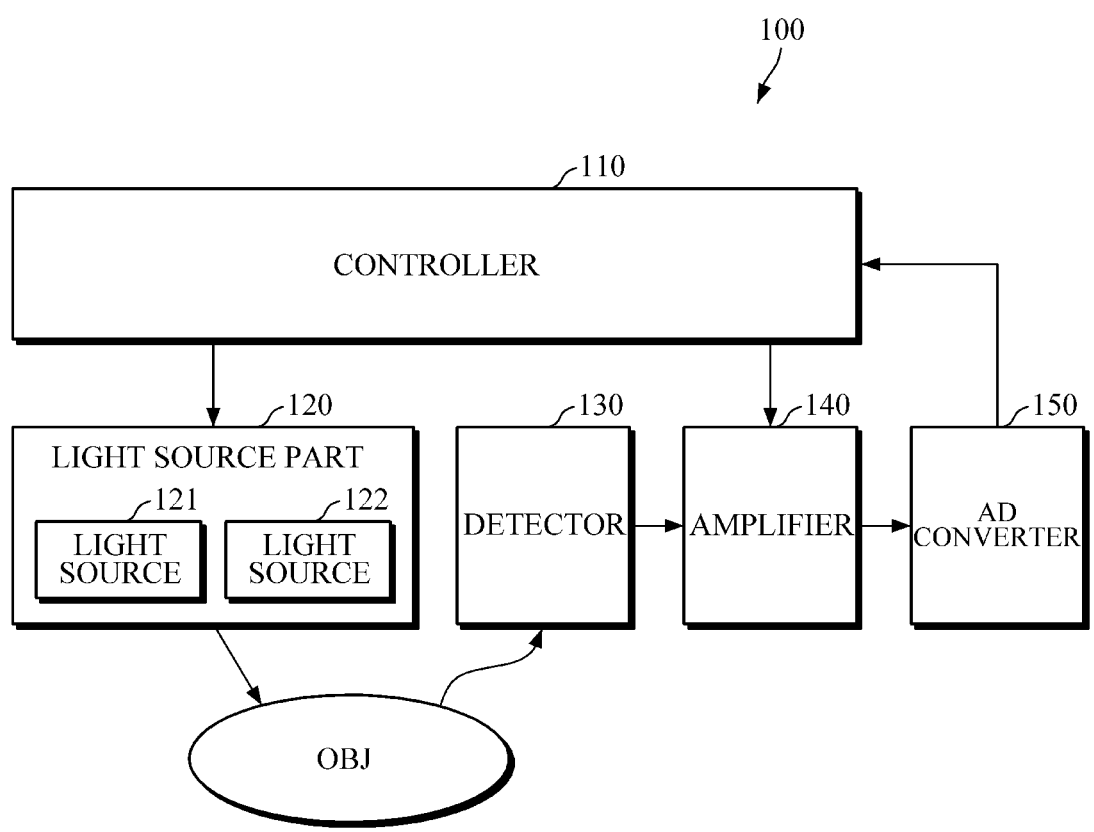
FIG. 1 is a block diagram illustrating a spectrometer.

Details of exemplary embodiments are included in the following detailed description and drawings. Advantages and features of exemplary embodiments, and methods of achieving the same will be more clearly understood from the following detailed description with reference to the accompanying drawings. Throughout the drawings and the detailed description, unless otherwise described, the same drawing reference numerals will be understood to refer to the same elements, features, and structures. The relative size and depiction of these elements may be exaggerated for clarity, illustration, and convenience.

It will be understood that, although the terms first, second, etc. may be used herein to describe various elements, these elements should not be limited by these terms. These terms are only used to distinguish one element from another. Any references to singular may include plural unless expressly stated otherwise.

In addition, unless explicitly described to the contrary, an expression such as "comprising" or "including" will be understood to imply the inclusion of stated elements but not the exclusion of any other elements. Also, the terms, such as "part", "'unit" or "'module", etc., should be understood as a unit that performs at least one function or operation and that may be embodied as hardware, software, or a combination thereof.

Hereinafter, exemplary embodiments of a spectrometer and a method of restoring a spectrum by the spectrometer will be described in detail with reference to the accompanying drawings.

Figure 2:
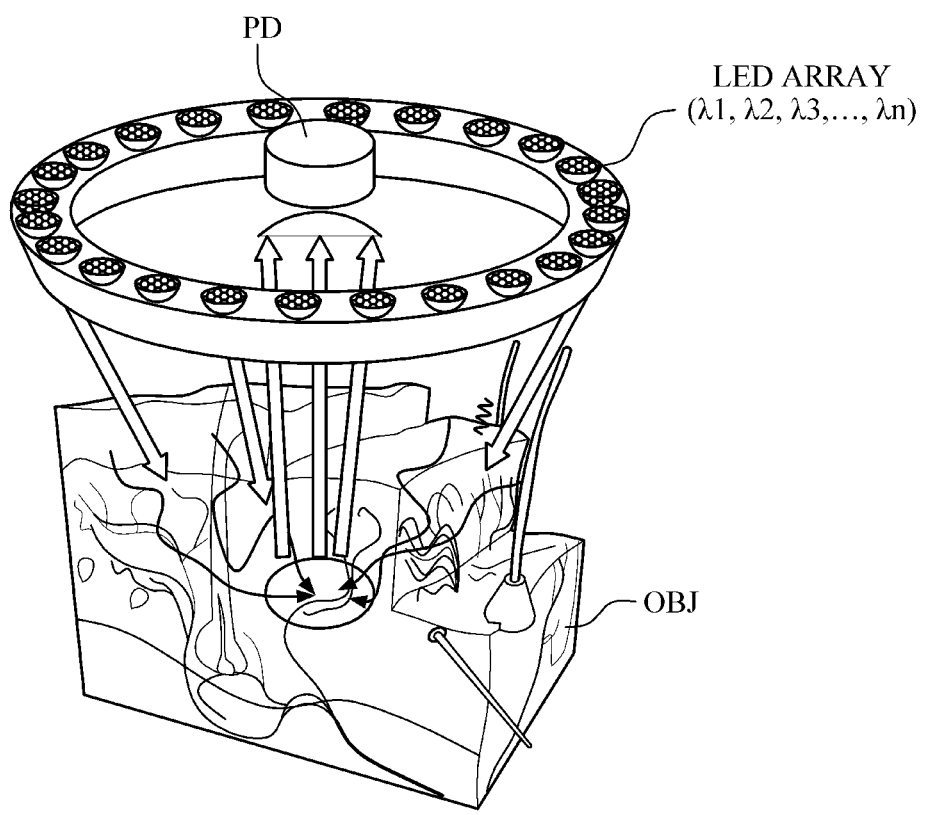
FIG. 2 is a diagram illustrating an example of a structure of a light source array of a spectrometer.

FIG. 1 is a block diagram illustrating a spectrometer, according to an exemplary embodiment. FIG. 2 is a diagram illustrating a structure of a light source array of a spectrometer, according to an exemplary embodiment.

Referring to FIG. 1, the spectrometer 1 includes a controller 110, a light source part 120, a detector 130, an amplifier 140, and a converter 150. In this case, the spectrometer 100 may be formed as a single hardware structure. However, the spectrometer 100 is not limited thereto, and at least some of the controller 110, the amplifier 140, and the converter 150 may be mounted in a different device that is physically separate, and may be mounted, for example, in a bio-information measuring apparatus.

The light source part 120 emits light in a plurality of wavelengths onto an object OBJ. As illustrated in the drawings, the light source part 120 may include a plurality of light sources 121 and 122 to emit light in the plurality of wavelengths. In this case, at least two of the plurality of light sources 121 and 122 may output light of different wavelengths. FIG. 1 illustrates the light source part 120 including only two light sources 121 and 122, but this is merely for convenience of explanation, and the number of light sources is not limited thereto. By the control of the controller 110, the light source part 120 may time-divide the output of light in the plurality of wavelengths, and may thus sequentially emit light of the different wavelengths onto the object OBJ. Each of light sources 121 and 122 may include any one or more of a light emitting diode (LED), a laser diode, a fluorescent body, or the like. The light sources 121 and 122 may emit near-infrared light, but are not limited thereto, and may also emit laser light for Raman spectroscopy.

Referring to FIG. 2, the light source part 120 may be an LED array having n-number of LEDs arranged on a circular frame. In this case, the LEDs may have peak wavelengths of $\lambda_1, \lambda_2, \lambda_3, \ldots,$ and $\lambda_n$. By the control of the controller 110, each LED may sequentially emit light of the wavelengths $\lambda_1, \lambda_2, \lambda_3, \ldots,$ and $\lambda_n$, respectively, onto the object OBJ by time-dividing the output of the light of the different wavelengths.

After light is emitted by each of the light sources 121 and 122 onto the object OBJ, the light is absorbed into, reflected or scattered from, the object OBJ depending on tissue properties of the object OBJ. In this case, photoreaction properties of the object OBJ may vary depending on the type of the object OBJ and the wavelengths of light, and a degree of light absorbed into, transmitted through, or reflected or scattered from the object OBJ may vary depending on the photoreaction properties of the object OBJ.

The detector 130 may detect an optical signal which is reflected by or scattered from the object OBJ. The detector 130 may convert the detected optical signal into an electric current signal, and may output the electric current signal. In this case, the detector 130 may include a photodiode, and may be an array having a plurality of photodiodes. Referring to FIG. 2, the detector 120 may include the photodiode (PD) disposed at the center of the circular frame on which the LEDs are arranged.

The amplifier 140 may amplify the electric current signal, output by the detector 130, with a predetermined amplification gain, and may output the amplified signal. In this case, the amplification gain may be set by synchronization with the operation of light sources. For example, at the time when the light source part 120 emits light of a specific wavelength, the amplification gain of the amplifier 140 may be set based on an optimal amplification gain which is pre-calculated for the specific wavelength. In this case, the time when the light source part 120 emits light of the specific wavelength may be before or after, or the same time as, the time when light of the specific wavelength is emitted.

The amplifier 140 may include one or more of a Trans-Impedance Amplifier (TIA), which converts the current signal output by the detector 130 into a voltage signal; and a Variable Gain Amplifier (VGA) which amplifies the voltage signal output from the TIA by using a set amplification gain and outputs the amplified voltage signal, in which the TIA and the VGA may be formed as a single part or as separate parts.

The converter 150 may convert an analog signal output from the amplifier 140 into a digital signal, and may output the digital signal. The converter 150 may have, as a system parameter, a maximum output value representative of a maximum value at which the digital signal may be output without saturating output of the amplifier 140.

The controller 110 may control each part of the spectrometer 100 by generating various control signals. Further, the controller 110 may receive an output signal from the converter 150, may reconstruct a spectrum based on the received output signal of the converter 150, and may perform various other operations.

For example, the controller 110 may control the light sources 121 and 122 of the light source part 110 to emit light onto the object. The controller 110 may time-divide and sequentially turn on or off one or more of the light sources 121 and 122 of the light source part 110. However, the controller 110 is not limited thereto, and may turn on or off all or some of the light sources at the same time, or may sequentially drive only some of the light sources.

Referring to FIG. 2, the controller 110 may turn on or off each of the LEDs of the LED array by time-dividing the LEDs so that each of the wavelengths $\lambda_1$, $\lambda_2$, $\lambda_3$, ..., and $\lambda_n$ may be sequentially emitted onto the object OBJ. For example, the controller 110 may control all the LEDs in such a manner that the controller 110 drives a first LED with a first light intensity for a first pulse duration, and after the first pulse duration elapses, the controller 110 turns off the first LED and drives a second LED with a second light intensity for a second pulse duration.

The controller 110 may set an amplification gain of the amplifier 140. The controller 110 may set an amplification gain, which is appropriate for a wavelength emitted by the light sources, by synchronizing operation of the amplifier 140 with the operation of the light sources. For example, at the time of driving the first LED which emits light of the wavelength $\lambda_1$, the controller 110 may set an amplification gain of the amplifier 140 based on an optimal amplification gain which is pre-calculated for the wavelength $\lambda_1$. Then, at the time of driving the second LED which emits light of the wavelength $\lambda_2$, the controller 110 may change the amplification gain of the amplifier 140 to an optimal amplification gain which is pre-calculated for the wavelength $\lambda_2$.

The controller 110 may calculate an optimal amplification gain for each wavelength of light to be emitted onto the object. For example, among amplification gains in a predetermined amplification gain section, the controller 110 may calculate, as an optimal amplification gain for a specific wavelength, a maximum amplification gain that does not saturate output of the converter 150 for the specific wavelength. An amplification gain that does not saturate the output of the converter 150 means that the amplification gain is not greater than a maximum output value of the converter 150 and does not saturate the output of the amplifier 140. The controller 110 may calculate an optimal amplification gain by sequentially changing the amplification gains from a minimum amplification gain to a maximum amplification gain in the amplification gain section. However, the calculation of the amplification gain is not limited thereto, and the controller 110 may select an amplification gain to be changed in the amplification gain section by using a binary search method or the like.

In another example, the controller 110 may directly calculate an optimal amplification gain based on a certain amplification gain set by the amplifier 140, a digital signal output by the converter 150 after being converted from a signal amplified by the amplifier 140 with the certain amplification gain, and a maximum output value of the converter 150.

Once the digital signal of each wavelength is output by the converter 150, the controller 110 may obtain a spectrum response for each wavelength based on the output digital signal of each wavelength. For example, the controller 110 may obtain a first spectrum response for each wavelength of the object based on the received digital signal of each wavelength. Since the obtained first spectrum response for each wavelength is a value scaled with a light intensity and an optimal amplification gain set for each wavelength, the controller 110 may restore the obtained first spectrum response for each wavelength to a second spectrum response for each wavelength corresponding to an originally intended light intensity and amplification gain.

Further, based on the obtained second spectrum response for each wavelength, the controller 110 may reconstruct a spectrum for measuring bio-information. For example, based on the second spectrum response for each wavelength, the controller 110 may obtain a linearly independent equation, and may reconstruct a spectrum based on the linearly independent equation. For example, the controller 110 may obtain a linear equation written in matrix form as represented by the following Equation 1 and may obtain the reconstructed spectrum by using a method of solving the linear equation.

$$Az = U \quad \text{[Equation 1]}$$

Herein, A is a matrix of reference spectrum properties measured according to driving conditions of each light source; U is a matrix of values actually measured by the detector according to driving conditions equally set for each light source; and z is a spectrum to be restored. In this case, there may be an ill-conditioned matrix A, in which a system value of Equation 1, which is a linear equation, may be incorrect, such that by using a solution to an inverse problem, a spectrum of an object may be reconstructed with no limitations on the resolution size of the spectrum, and with high accuracy by using a minimum number of spectrum curves.

The Tikhonov regularization method used to solve the inverse problem may be represented by the following Equation 2.

$$(\alpha E + A^T A)Z_\alpha = A^T u$$

$$Z_\alpha = (\alpha E + A^T A)^{-1} A^T u \quad \text{[Equation 2]}$$

Herein, u is each component of a matrix U actually measured by the detector; E is a unit matrix; A is a kernel matrix, and a matrix of a reference spectrum measured for each light source according to driving conditions of the light sources; and $\alpha$ is a unit of noise removal. The Equation 2 may be solved by a known method, e.g., a least square method, which may be solved by using, for example, QR decomposition.

Figure 3:
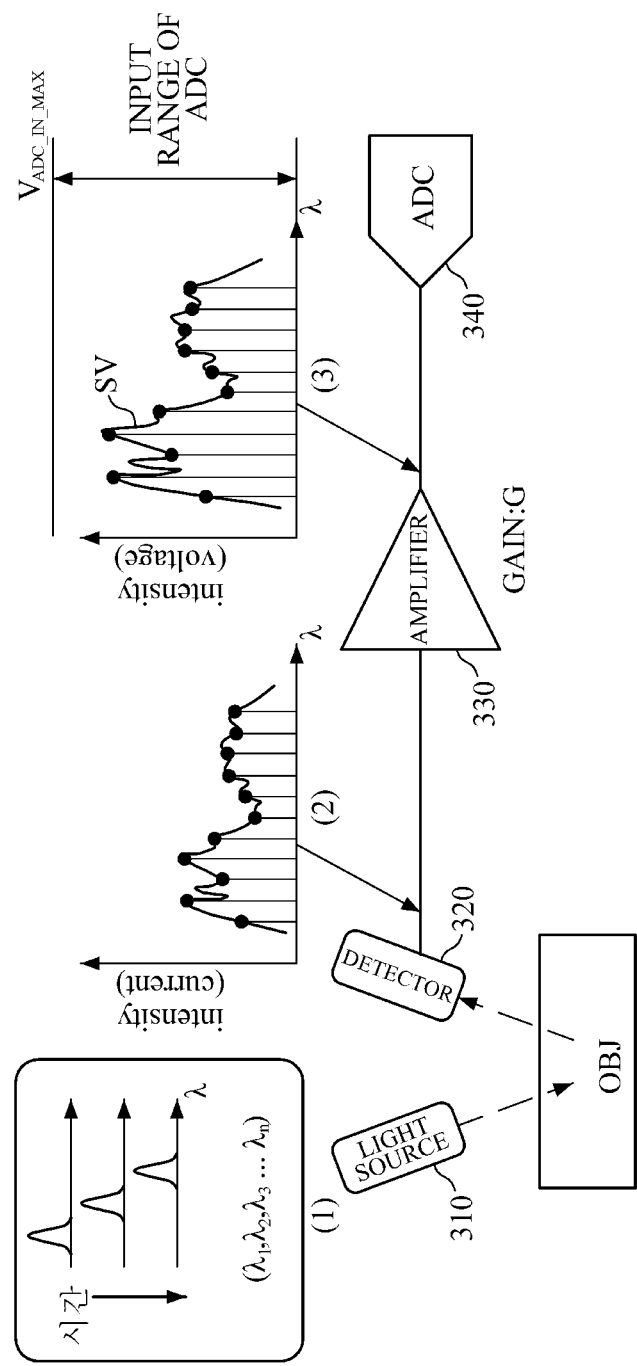
FIG. 3 is a circuit diagram explaining a related art spectrometer.
Figure 4A:
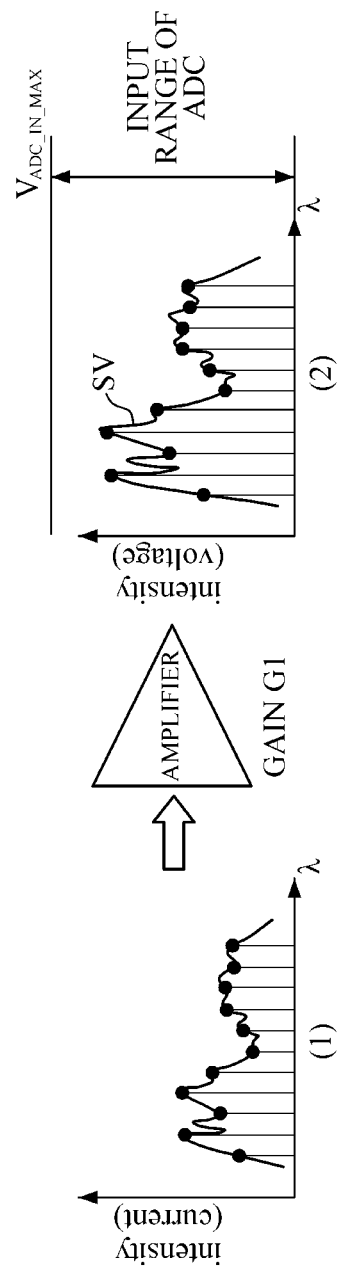
FIGS. 4A and 4B are diagrams explaining adjusting an output gain of a spectrometer, according to exemplary embodiments.
Figure 4B:
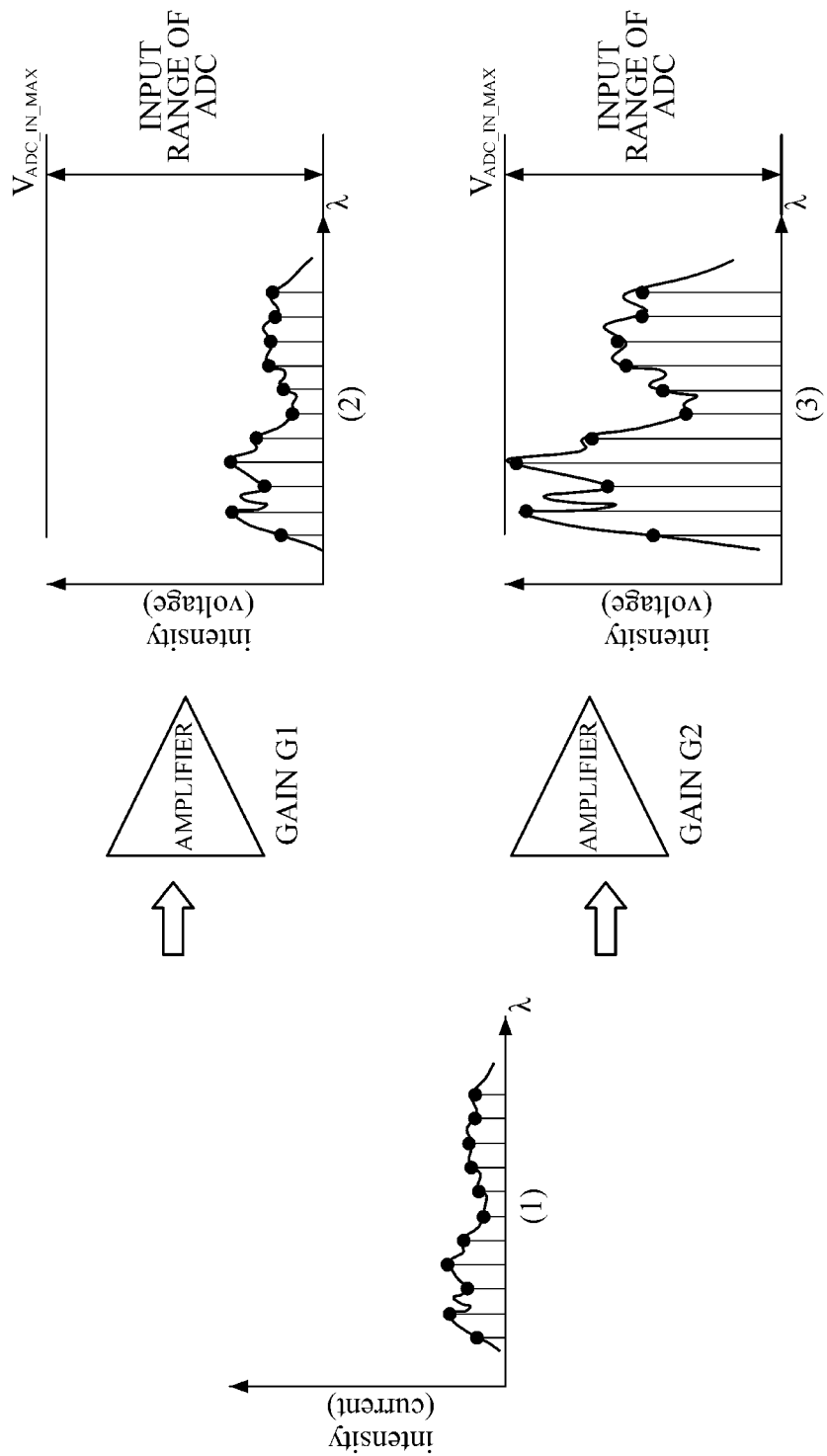
Figure 5:
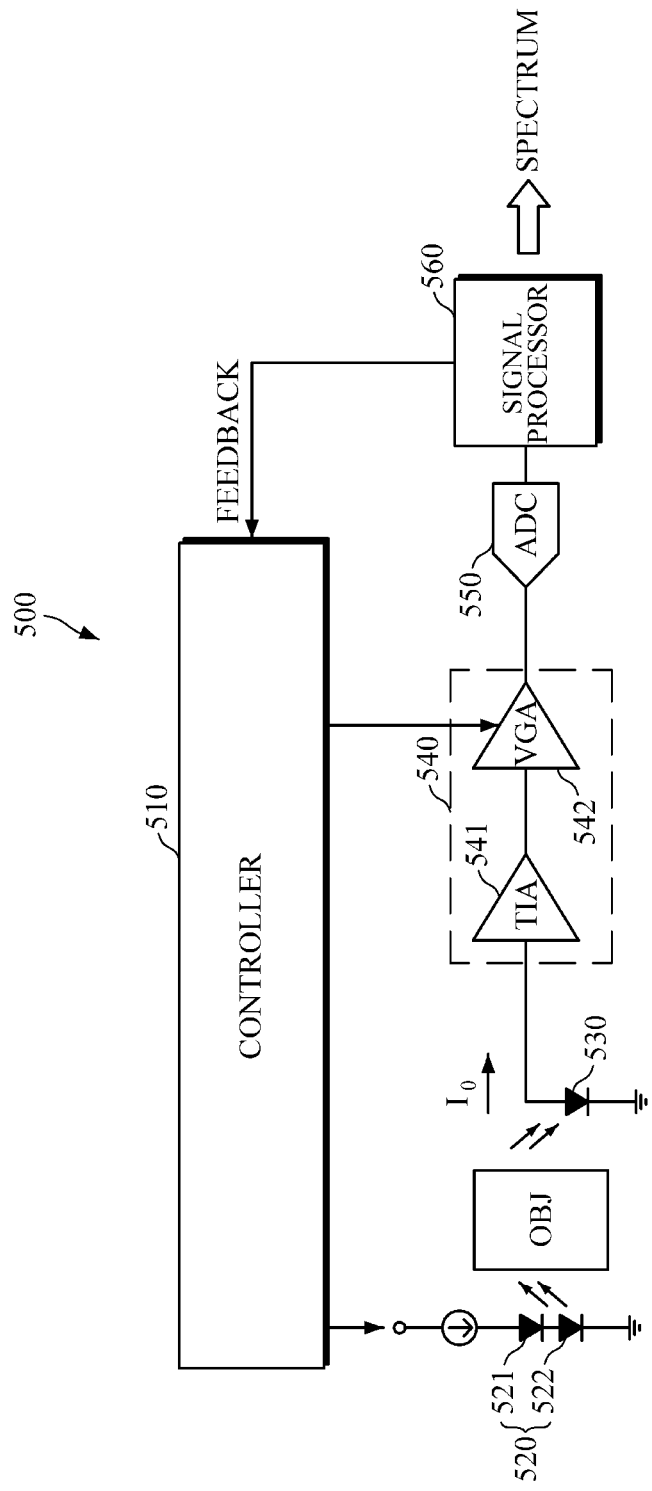
FIG. 5 is a circuit diagram illustrating a spectrometer, according to an exemplary embodiment.

FIG. 3 is a circuit diagram explaining a related art spectrometer. FIGS. 4A and 4B are diagrams explaining adjusting an output gain of a spectrometer, according to an exemplary embodiment. FIG. 5 is a circuit diagram illustrating a spectrometer according to an exemplary embodiment.

Referring to FIGS. 3 to 5, an operating principle of a spectrometer according to an exemplary embodiment will be described in further detail.

Referring to FIG. 3, in a related art spectrometer system, once a light source 310 (1) sequentially emits successive wavelengths onto an object OBJ, (2) a detector 320 detects light, reflected by or scattered from the object OBJ according to absorbance properties of the object OBJ for each wavelength, and outputs the light into an electric current signal. (3) The electric current signal of the detector 320, which is proportional to a received light amount, is converted into a voltage signal by an amplifier 330, and is amplified with an amplification gain G to be input to an ADC 340. The ADC 340 converts the input voltage signal into a digital signal, and outputs the digital signal. The output signal of the ADC 340 is used to restore the spectrum of the object OBJ.

In this case, in order to minimize a quantization noise of the ADC 340, it is required to set the amplification gain G to be close to a maximum output value ($V_{ADC\_IN\_MAX}$) which is within an input range of the ADC 340, but not greater than the maximum output value ($V_{ADC\_IN\_MAX}$), so that an amplification signal of the amplifier 330 is not saturated.

Accordingly, in this related art spectrometer system, when measuring various objects having different levels of reflectivity, the magnitude of the amplification gain for all objects is limited to an amplification gain for an object having the highest reflectivity, which satisfies the above-described conditions. Further, even the same object may have different photoreaction properties for each wavelength, such that in the case in which a spectrum is measured by sequentially emitting light of a plurality of wavelengths onto the same object, the magnitude of an amplitude gain for all the wavelengths is limited to the amplitude gain for the wavelength having the highest reflectivity.

FIG. 4A illustrates an example of a current signal (1) output by the detector for an object or a wavelength having a relatively high reflectivity, and a signal (2) output by the amplifier by amplifying the current signal (1) with the amplification gain G1. As illustrated in FIG. 4A, while the output signal (2) of the amplifier has a value within an input range of the ADC so that the output of the ADC is not saturated, the amplification gain G1 may be set to a value close to a maximum output value ($V_{ADC\_IN\_MAX}$) in order to minimize a quantization noise of the ADC.

FIG. 4B illustrates an example of amplifying a current signal (1) output by the detector for an object or a wavelength having a relatively low reflectivity. The amplification signal (2) of FIG. 4B is a signal amplified with an amplification gain G1 which is set for the case of the high reflectivity in FIG. 4A. As illustrated in FIG. 4B, since the amplification gain G1 of the amplifier is set for the case of a high reflectivity, the amplification signal (2) of the amplifier is not close to the maximum output value ($V_{ADC\_IN\_MAX}$) when measuring an object or a wavelength having a low reflectivity. In this case, the quantization noise is increased as compared to a case of a wavelength having a high reflectivity, thereby imposing limitations on the accurate restoration of a spectrum.

In contrast, in FIG. 4B, an amplification signal (3) is obtained by amplifying the current signal (1), having a lower reflectivity than the amplification signal (2), with an amplification gain G2 which is relatively greater than the amplification gain G1. In this case, a value of the amplification gain G2 is calculated so that the output of the amplification signal (3) may be close to the maximum output value ($V_{ADC\_IN\_MAX}$) of the ADC in consideration of the reflectivity of the current signal (1), thereby minimizing the quantization noise of the ADC without saturating the amplification signal (3) of the amplifier as illustrated in FIG. 4B.

Referring to FIG. 5, the spectrometer 500, according to an exemplary embodiment, includes a controller 510, a light source part 520, a detector 530, an amplifier 540, a converter 550, and a signal processor 560. In this case, the controller 510 and the signal processor 560 are illustrated as two parts, which are merely separated according to functions, and may, alternately, be included in a single controller as illustrated in FIG. 1.

Upon receiving a control signal for obtaining a spectrum of an object from the signal processor 560, the controller 510 may drive the light source part 520. The light source part 520 may be, for example, an array of n number of LEDs: $LED_1$, $LED_2$, ..., and $LED_N$, which emit light of n number of wavelengths $\lambda_1$, $\lambda_2$, ..., and $\lambda_n$, respectively. FIG. 5 illustrates two LEDs, $LED_1$ 521 and $LED_2$ 522, but this is merely for convenience of explanation, and the number of LEDs included in the LED array is not limited thereto.

Further, at the time of driving the LEDs 521 and 522, the controller 510 may set an amplification gain of a VGA 542 of the amplifier 540 based on an optimal amplification which is pre-calculated for the wavelength of each of the LEDs 521 and 522. In this case, the controller 510 may set the amplification gain of the VGA 542 before and after the time of driving the LEDs 521 and 522.

For example, in a case in which the optimal amplification gains $G_{opt,1}$, $G_{opt,2}$, ..., and $G_{opt,n}$ are pre-calculated for each of the wavelengths $\lambda_1$, $\lambda_2$, ..., and $\lambda_n$, respectively, the controller 510 drives the first $LED_1$ 521 with a light intensity $I_{0,1}$, and may set the optimal amplification gain $G_{opt,1}$, which is pre-calculated for the wavelength by synchronization with the operation of the LED, as an amplification gain of the VGA 542.

When light of the wavelength $\lambda_1$ emitted by the first $LED_1$ 521 is absorbed, transmitted, reflected, or scattered according to tissue properties of the object OBJ, the detector 530 detects an optical signal, converts the detected optical signal into an electric current signal, and outputs the electric current signal. In this case, the detector 530 may be a photodiode.

The current signal output by the detector 530 is input into the TIA 541 of the amplifier 540 to be converted into a voltage signal, is amplified with the optimal amplification gain of the wavelength $\lambda_1$ by the VGA 542, and is output. The output amplified signal is amplified with the optimal amplification gain of the wavelength $\lambda_1$, such that the output amplification signal is not saturated but may be output as a value close to a maximum output value of the converter 550.

The converter 550 converts the input analog amplified signal into a digital signal, and transmits the digital signal to the signal processor 560. The converter 550 may include an AD converter (ADC).

The controller 510 drives the second $LED_2$ 522 with a light intensity of $I_{0,2}$, and may set the optimal amplification gain $G_{opt,2}$, which is pre-calculated for the wavelength $\lambda_2$, by synchronization with the operation of the LED, as an amplification gain of the VGA 542 of the amplifier 540. The detector 530, the amplifier 540, and the converter 550 may repeat the above-described detection, amplification, and conversion each time one of the wavelengths $\lambda_1$, $\lambda_2$, ..., and $\lambda_n$ is emitted. In this case, the light intensity of each LED may be calculated when the optimal amplification gain is used.

The signal processor 560 may restore a spectrum based on the digital signal transmitted from the converter 550. For example, once the digital signal is output by the converter 550 for a wavelength $\lambda_i$ ($1 \leq i \leq n$, i being an integer), the signal processor 560 may obtain a first spectrum response $X_i$ for each wavelength detected from the object OBJ based on the output digital signal. In this case, the first spectrum response $X_i$ for each wavelength is a value scaled with a different light intensity $I_{0,i}$ and a different amplification gain $G_{opt,i}$ for each wavelength, such that the first spectrum response $X_i$ may be restored to a second spectrum response $Y_i$, which is originally intended to be obtained, by using the following Equation 3, in which k is a certain constant predefined through preprocessing.

$$Y_i = k \frac{X_i}{G_{opt,i} I_{0,i}} \qquad \text{[Equation 3]}$$

As described above, the signal processor 560 may reconstruct a spectrum based on the obtained second spectrum response for each wavelength, and may output the reconstructed spectrum to a bio-information measuring apparatus or an external device such as an external display device.

Upon receiving a request to calculate an optimal amplification gain for each wavelength from a user or other device, the signal processor 560 may calculate the optimal amplification gain for each wavelength with respect to the object OBJ. Further, upon receiving a request to obtain a spectrum of the object OBJ from a user or other device, the signal processor 560 may determine whether to re-calculate the optimal amplification gain for each wavelength based on whether the object has been changed, whether a wavelength to be emitted onto the object has changed, and the like. Further, if a digital signal is output by the converter 550 when measuring a spectrum of the object OBJ, the signal processor 560 may determine whether to re-calculate an optimal amplification gain for a specific wavelength based on whether an output signal for the specific wavelength is saturated.

Upon determining to re-calculate the optimal amplification gain, the signal processor 560 transmits a control signal to the controller 510. Upon receiving the control signal, the controller 510 may drive an LED$_i$, to emit light of a wavelength $\lambda_i$ with a light intensity $I_{0,i}$.

While the LED$_i$ emits light onto the object OBJ, the controller 510 may change the amplification gains $G_1$, $G_2$, ..., and $G_M$ of the VGA of the amplifier 540 in a predetermined amplification gain section. For example, the controller 510 may sequentially increase the amplification of the VGA from a minimum amplification gain $G_1$ to a maximum amplification gain $G_M$ in the amplification gain section. Alternatively, the controller 510 may set an amplification gain of the VGA by selecting an amplification gain in the amplification gain section using a binary search method. But the amplification gain is not limited thereto.

The signal processor 560 may calculate the optimal amplification gain for a wavelength $\lambda_i$ based on a signal output by the amplifier 540 or the converter 550 according to the changed amplification gain. For example, from among the changed amplification gains, the signal processor 560 may determine a maximum amplification gain, which does not saturate the output of the amplifier 540, to be the optimal amplification gain $G_{opt,i}$ for the wavelength $\lambda_i$. In the case in which the determined optimal amplification gain $G_{opt,i}$ is equal to the maximum amplification gain $G_M$ in the amplification gain section, the signal processor 560 increases the light intensity $I_{0,i}$ of the LED$_i$ for the wavelength $\lambda_i$ by a predetermined level, and may control the controller 510 again to re-calculate the optimal amplification gain for the wavelength $\lambda_i$ with the increased light intensity.

However, the method of calculating the optimal amplification gain for the wavelength $\lambda_i$ is no limited thereto. For example, the signal processor 560 may directly obtain the optimal amplification gain by using the following Equation 4 based on an amplification gain set by the amplifier 540, an output value amplified with the set amplification gain and output by the converter 550, and a maximum output value of the converter 550.

$$G_{opt} = G_a \times \frac{Y_{MAX}}{Y_{ADC0}} \qquad \text{[Equation 4]}$$

Herein, $G_a$ is an amplification gain set by the amplifier 540, $Y_{ADC0}$ is an output value of the converter 550, and $Y_{MAX}$ is a maximum value that may be obtained by the output of the converter 550 without saturating an amplified signal.

Upon calculating the light intensity and optimal amplification gain for each wavelength, the signal processor 560 may transmit feedback information to the controller 510 under the light source driving condition.

Figure 6:
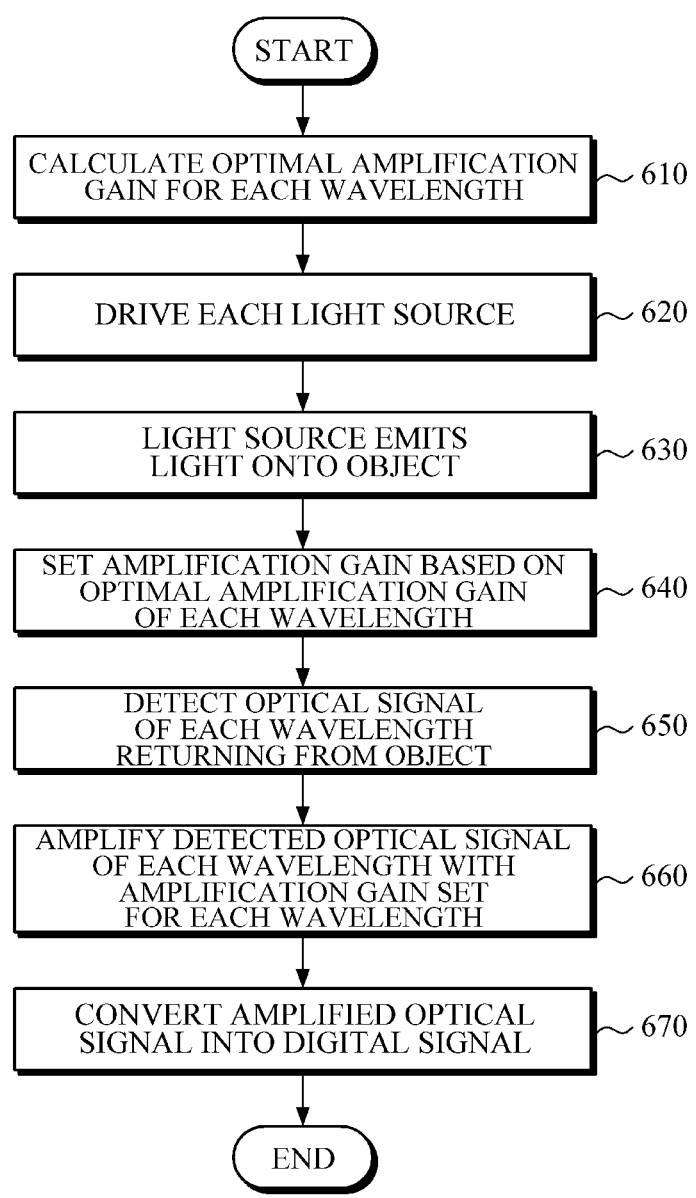
FIG. 6 is a flowchart illustrating a method of obtaining a spectrum using a spectrometer, according to an exemplary embodiment.
Figure 7:
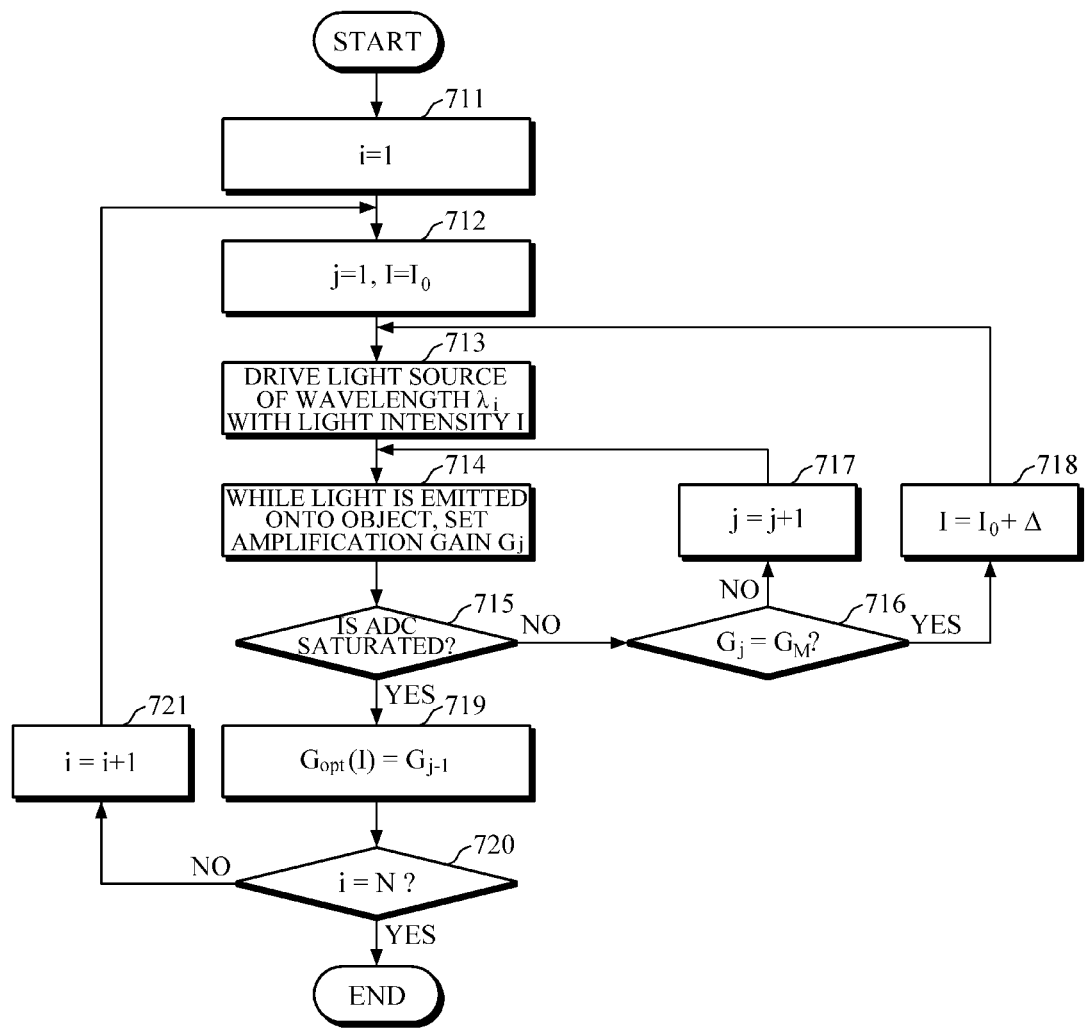
FIG. 7 is a flowchart illustrating calculating an optimal amplification gain for each wavelength, according to an exemplary embodiment.

FIG. 6 is a flowchart illustrating a method of obtaining a spectrum by a spectrometer, according to an exemplary embodiment. FIG. 7 is a flowchart illustrating a method of calculating an optimal amplification gain for each wavelength, according to an exemplary embodiment. The methods of FIGS. 6 and 7, together, are one example of a spectrum obtaining method performed by the spectrometer 100 of FIG. 1.

Upon receiving a request to measure a spectrum of an object, the controller 110 may calculate an optimal amplification gain for each wavelength in 610. In this case, the spectrum measuring request may be received from a user or from another device. Upon receiving the spectrum measuring request, the controller 110 may determine whether to calculate the optimal amplification gain. Based on a determination that the optimal amplification gain does not need to be calculated, the controller 110 may omit the calculation of the optimal amplification gain for one or more wavelengths in 610.

FIG. 7 illustrates calculating the optimal amplification gain, according to an exemplary embodiment. Referring to FIG. 7, the controller 110 sets a wavelength index i to be 1 to calculate an optimal amplification gain for a first wavelength $\lambda_1$ in 711.

The controller 110 sets a first amplification gain index j to be 1 to sequentially change amplification gains $G_1$, $G_2$, ..., and $G_M$ of the amplifier 140 in a predetermined amplification gain section, and sets a light intensity I of a light source, which emits light of the wavelength $\lambda_1$, to be $I_0$ in 712.

the controller 110 drives the light source of the wavelength $\lambda_1$ with the light intensity I in 713, and while light is emitted onto the object, sets the amplification gain of the amplifier 140 to be the amplification gain $G_j$ in 714.

In 715, controller 110 may determine whether a signal amplified by the amplifier 140 saturates an output of the ADC.

If the amplification signal of the amplifier 140 is not saturated, the controller 110 may determine whether the current amplification gain $G_j$ is equal to the maximum amplification gain $G_M$ in 716.

In response to the current amplification gain $G_j$ being equal to the maximum amplification gain $G_M$ in the amplification gain section, the controller 110 increases the light intensity I of the wavelength $\lambda_1$ by a predetermined level $\Delta$ in 718, and proceeds to 713. In response to the current amplification gain $G_j$ not being equal to the maximum amplification gain $G_M$ in the amplification gain section, in 716, the controller 110 increases a next amplification gain index j by 1 in 717, and proceeds to 714. If the amplification signal of the amplifier 140 is saturated for the current amplification gain $G_j$, in 715, the controller 110 may determine, in 719, that the optimal amplification gain $G_{opt}$ for the wavelength $\lambda_1$ is a previous amplification gain $G_{j-1}$.

In 720, the controller 110 compares whether the current wavelength index i is equal to the last wavelength index N; and in response to the current wavelength index i not being equal to the last wavelength index N, the controller 110 increases the wavelength index i by 1 in order to calculate the optimal amplification gain for a next wavelength, and proceeds to 712. Upon comparison, if the current wavelength is the last wavelength, the controller 110 ends the process.

Referring back to FIG. 6, the controller 110 drives the light source part 120 in 620 with the light intensity obtained for each wavelength in 610.

In 630, the light source part 120 drives the light source by the control of controller 110 to emit light onto the object.

In 640, when light of each wavelength is emitted onto the object by the light source part 120, the controller 110 may set an amplification gain of the amplifier 140 based on the optimal amplification gain calculated in 610 for each wavelength.

In 650, the detector 130 may detect an optical signal of each wavelength returning from the object, and may output an electric signal.

In 660, the amplifier 140 may amplify the output electric signal for each wavelength with an amplification gain set for each wavelength in 640, and may output the amplified signal. In this case, the amplifier 140 may convert the electric current signal, output in 650, into a voltage signal, and may amplify and output the voltage signal.

In 670, the converter 150 may convert the amplified analog signal into a digital signal, and may output the digital signal. In this case, the signal input to the converter 150 is a signal amplified with an optimal amplification gain in consideration of the reflectivity of an object for each wavelength, such that the converter 150 may output a signal which may minimize a quantization noise level without being saturated.

The controller 150 may restore a spectrum based on the output digital signal.

Hereinafter, exemplary embodiments of an apparatus and method for measuring bio-information will be described in detail with reference to the following drawings.

Figure 8:
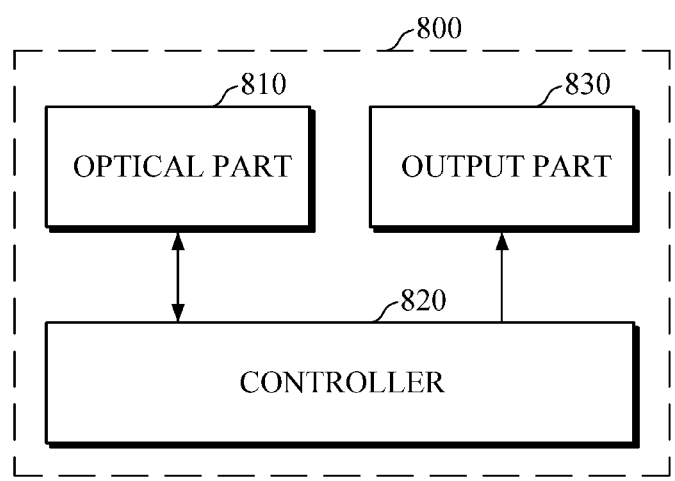
FIG. 8 is a block diagram illustrating a bio-information measuring apparatus, according to an exemplary embodiment.
Figure 9:
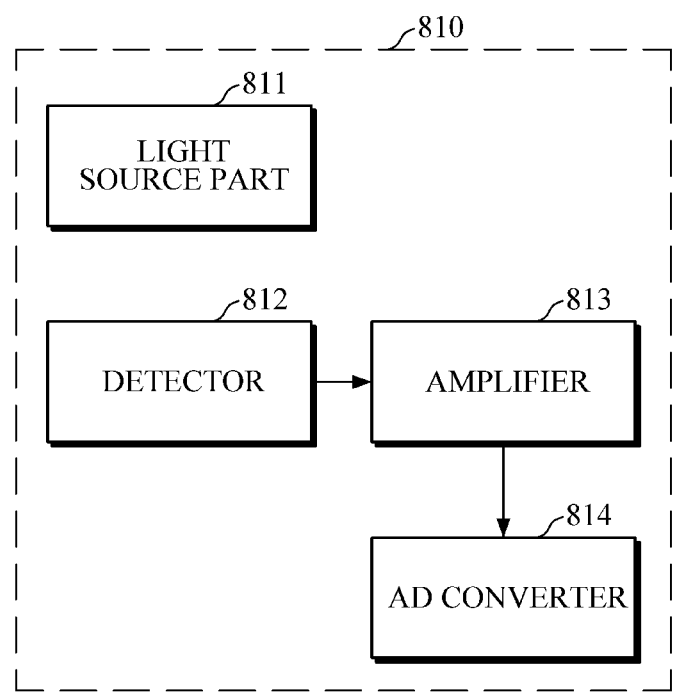
FIG. 9 is a block diagram illustrating a spectrometer part of a bio-information measuring apparatus, according to an exemplary embodiment.
Figure 10:
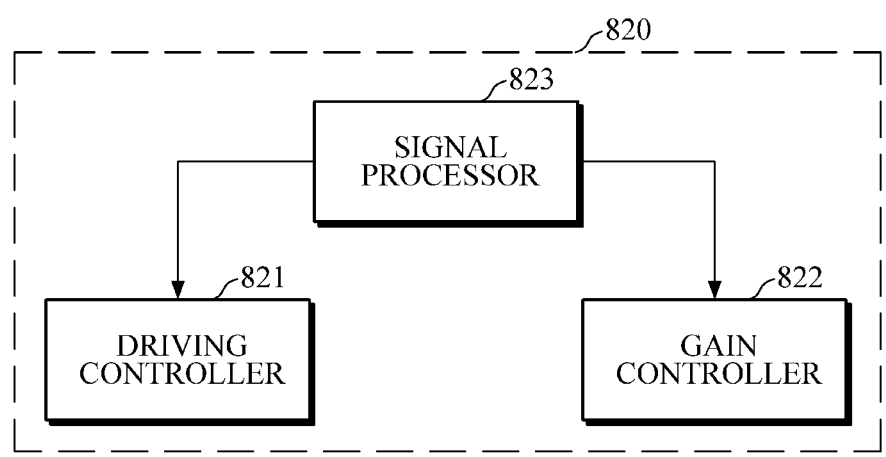
FIG. 10 is a block diagram illustrating a controller of a bio-information measuring apparatus, according to an exemplary embodiment.

FIG. 8 is a block diagram illustrating a bio-information measuring apparatus, according to an exemplary embodiment. FIG. 9 is a block diagram illustrating a spectrometer part of a bio-information measuring apparatus, according to an exemplary embodiment. FIG. 10 is a block diagram illustrating a controller of a bio-information measuring apparatus, according to an exemplary embodiment.

The bio-information measuring apparatus 800 may be an apparatus for measuring any of various types of information including blood glucose, triglyceride, cholesterol, calories, protein, uric acid, and the like. The bio-information measuring apparatus 800 may be manufactured as a watch-type device illustrated in FIG. 13A. However, the bio-information measuring apparatus 800 is not limited thereto, and may be not only a wristband-type device, a bracelet-type device, a ring-type device, a glasses-type device, a hairband-type device or the like, but may also be manufactured in any of various sizes and shapes according to a measurement purpose of bio-information or a place of use of the bio-information measuring apparatus.

Referring to FIG. 8, the bio-information measuring apparatus 800 includes an optical part 810, a controller 820, and an output part 830. The optical part 810 and the controller 820 in this exemplary embodiment may perform the functions of the spectrometers 100 and 500 illustrated in FIGS. 1 and 5.

The optical part 810 emits light onto an object under the control of the controller 820, detects an optical signal from the object according to photoreaction properties of the object, processes the detected optical signal, and transmits the processed optical signal to the controller 820.

Upon receiving any of various commands related to measurement of bio-information from a user, the controller 820 may control the optical part 810 and the output part 830, and may measure bio-information based on the signal processed and output by the optical part 810.

The output part 830 may output a processing result of the optical part 810 and the controller 820 to a user through any of various output modules by using any of various visual or non-visual methods. For example, the output module may be a display module which visually displays the processing result, a speaker module which outputs the processing result in voice, or a haptic module which outputs the processing result through vibration, tactility, or the like, but is not limited thereto.

Referring to FIG. 9, the optical part 810 includes a light source part 811, a detector 812, an amplifier 813, and a converter 814.

The light source part 811 may include one or more light sources, and may emit light by time-dividing the outputting of light of each wavelength according to the control of the controller 820.

The detector 812 may include a photodiode, and may detect light reflected or scattered to the detector 812 after being emitted onto the object by the light source part 811, may convert the detected optical signal into an electric current signal, and may output the electric current signal.

The amplifier 813 may convert the electric signal output by the detector 812 into a voltage signal, may amplify the voltage signal with a predetermined amplification gain, and may output the amplified voltage signal. In this case, at the time of driving a light source of each wavelength, the controller 820 may set or change the amplification gain of the amplifier 813 based on an optical amplification gain for each wavelength, respectively.

The converter 814 may convert the analog signal, amplified and output by the amplifier 813, into a digital signal and may transmit the digital signal to the controller 820.

Referring to FIG. 10, the controller 820 may include a driving controller 821, a gain controller 822, and a signal processor 823.

The signal processor 823 may receive a request for measuring bio-information. In this case, the request for measuring bin-information may be received from a user or from an external device.

Upon receiving the bio-information measuring request, the signal processor 823 may determine whether to calculate an optimal amplification gain for each wavelength of light to be emitted onto the object. For example, upon receiving the bio-information measuring request, the signal processor 823 may collect one or more of information on the object to be measured and sensor information, and may determine whether to calculate the optimal amplification gain by using the collected information. The information on the object to be measured may include a user's gender, age, and health state, and information on a portion to be examined that is contacted by the optical part 810. Further, the sensor information may include information collected from a tilt sensor, a contact pressure sensor, or the like which is mounted in the bio-information measuring apparatus 800. For example, in the case in which a health state, a contact pressure, or a portion to be examined of a user is different from previous data, the reflectivity of the object for each wavelength may be different from previous reflectivity, such that the signal processor 823 may determine to calculate the optimal amplification gain for each wavelength.

Upon determining to calculate the optimal amplification gain for each wavelength, the signal processor 823 may set an initial light intensity and an amplification gain section for each wavelength, and may generate a control signal to the driving controller 821 and the gain controller 822.

Once the driving controller 821 drives the light source part 811 with the initial light intensity set for each wavelength, the light source part 811 may time-divide light sources and may sequentially drive each light source to emit light.

While the light source emits light of a specific wavelength, the gain controller 822 may change an amplification gain of the amplifier 813 within a predetermined amplification gain section.

The signal processor 823 may determine whether each amplification gain, which is changed by the gain controller 822 within the amplification gain section, saturates an amplification signal of the amplifier 813, and may determine, as an optimal amplification gain for the specific wavelength, a maximum amplification gain among amplification gains that do not saturate the amplification signal. In this case, if the determined optimal amplification gain is equal to the maximum amplification gain in the amplification gain section, the signal processor 823 may increase the light intensity for the specific wavelength, and may repeat the process of calculating the optimal amplification gain. However, the calculation of the optimal amplification gain is not limited thereto, and the signal processor 823 may calculate the optimal amplification gain in any of various other methods as described above.

Upon determining the light intensity and the optimal amplification gain for each wavelength in this manner, the signal processor 823 may manage the determined light intensity and optimal amplification gain in a storage device under the light source driving condition. The light source driving condition may further include information on a driving order, a pulse duration, and the like, in addition to the light intensity and the optimal amplification gain for each wavelength.

The storage device may include at least one storage medium of a flash memory type memory, a hard disk type memory, a multimedia card micro type memory, a card type memory (e.g., a Secure Digital (SD) memory, an eXtreme Digital (XD) memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, an optical disk, or the like, but is not limited thereto.

Upon determining not to calculate the optimal amplification gain for each wavelength, or upon completing calculation of the optimal amplification gain, the signal processor 823 may control the driving controller 821 and the gain controller 822 for measuring bio-information. The driving controller 821 may control the light source part 811 by referring to the light source driving condition; and when light of each wavelength is emitted, the gain controller 822 may set, as an amplification gain of the amplifier 813, an optimal amplification gain of the emitted wavelength by referring to the light source driving condition.

Once a digital signal for each wavelength is output by the converter 814, the signal processor 823 may reconstruct a spectrum of an object based on the output digital signal. As described above, the signal processor 823 may obtain a response for each wavelength based on the digital signal output from the converter 814, and may reconstruct the spectrum based on the obtained response for each wavelength. The spectrum reconstruction may be performed by using the above-described Equations 1 and 2. In this case, the spectrum response obtained based on the digital signal output by the converter 814 is a value scaled with a different light intensity and a different amplification gain for each wavelength, such that the signal processor 823 may restore the spectrum response to an originally intended spectrum response for each wavelength by using the method of Equation 3, and may reconstruct the spectrum based on the restored spectrum response.

Upon reconstructing the spectrum of the object, the signal processor 823 may measure bio-information by using the reconstructed spectrum and a pre-defined bio-information measurement model. In this case, the bio-information measurement model may be pre-defined as a linear function model, but is not limited thereto.

Upon measuring the bio-information, the signal processor 823 may analyze the measured bio-information, and may generate health state information of a user, an alarm, warning information, or the like.

Figure 11:
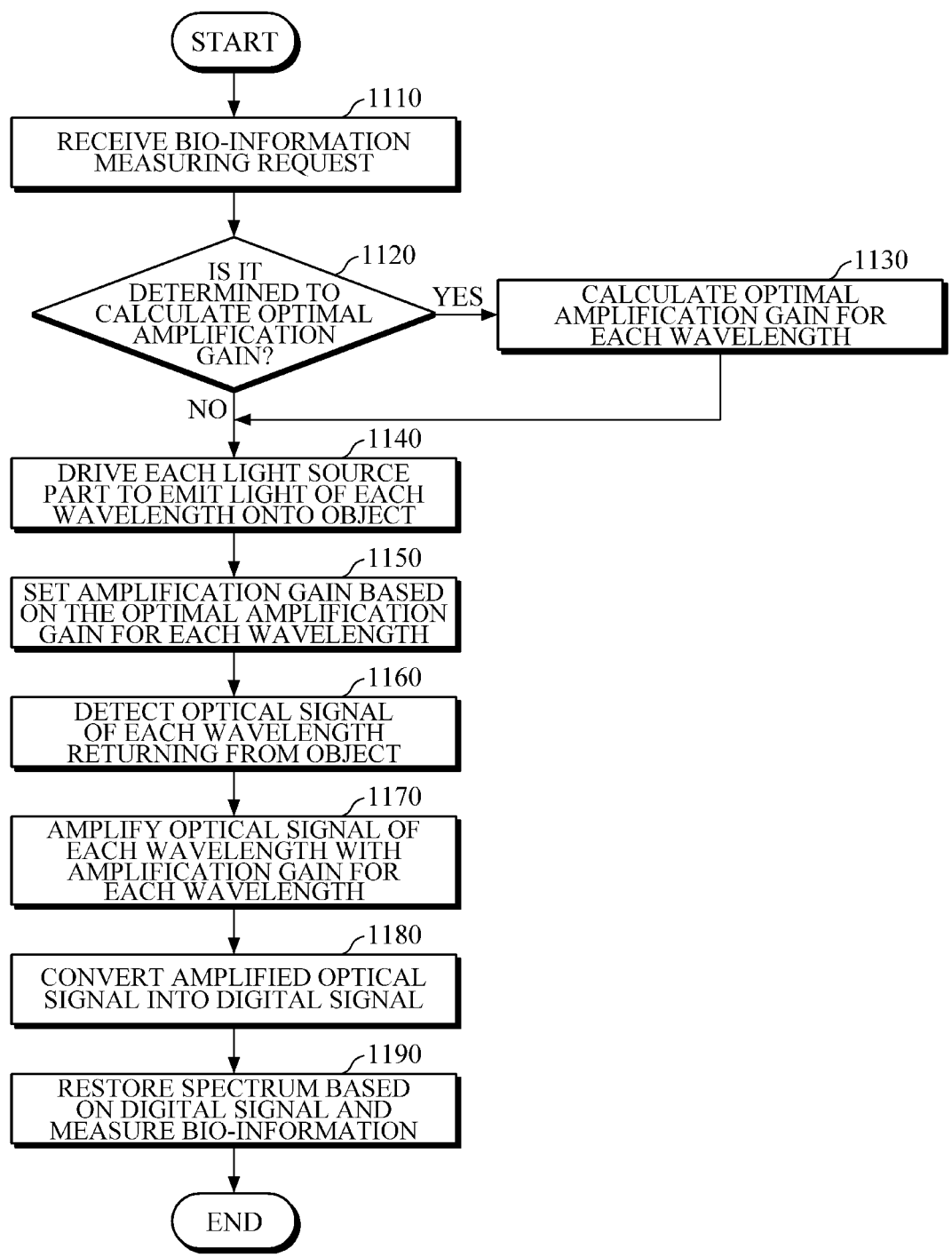
FIG. 11 is a flowchart illustrating a bio-information measuring method, according to an exemplary embodiment.
Figure 12:
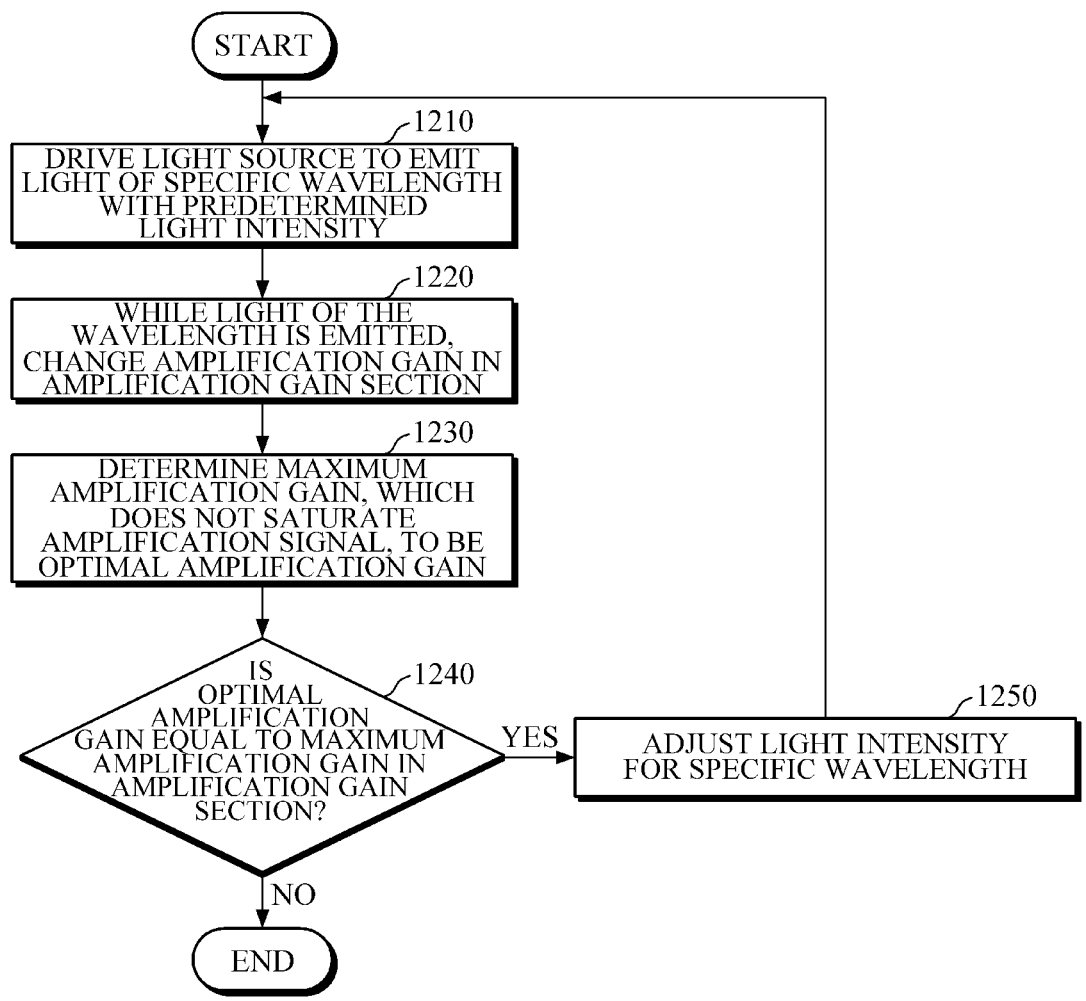
FIG. 12 is a flowchart illustrating a method of an optimal amplification gain, according to an exemplary embodiment.

FIG. 11 is a flowchart illustrating a bio-information measuring method, according to an exemplary embodiment. FIG. 12 is a flowchart illustrating a method of calculating an optimal amplification gain, according to an exemplary embodiment.

FIGS. 11 and 12 may, together, be an example of a bio-information measuring method performed by the bio-information measuring apparatus 800 of FIG. 8.

Referring to FIG. 11, the controller may receive a bio-information measuring request in 1110, and may determine whether to calculate an optimal amplification gain for each wavelength in 1120. For example, upon receiving the bio-information measuring request, the controller collects one or more of information on the object and sensor information, and determines whether information on a health state, a contact pressure, a portion to be examined of a user, or the like is different from previous data. Upon determination that the information is different from the previous data, the controller may determine to calculate an optimal amplification gain for each wavelength, since reflectivity of the object for each wavelength may be different from a previous reflectivity.

Upon determining to calculate the optimal amplification gain for each wavelength in 1120, the controller may calculate the optimal amplification gain for each wavelength in 1130.

Referring to FIG. 12, as an exemplary embodiment of calculating the optimal amplification gain in 1130, the controller may drive a spectrometer part to emit light of a specific wavelength with a predetermined light intensity onto an object in 1210.

In 1220, while light of the specific wavelength is emitted onto the object, the controller may change an amplification gain of a variable gain amplifier (VGA) in a predetermined amplification gain section.

In 1230, among the amplification gains changed in 1220, the controller may determine a maximum amplification gain, which does not saturate an amplification signal of the VGA, to be the optimal amplification gain for the specific wavelength.

In 1240, the controller determines whether the determined optimal amplification gain is equal to the maximum amplification gain in the amplification gain section; and if they are equal, in 1250, the controller may increase the light intensity for the specific wavelength, and may repeat the operation 1210 and the following operations. If they are not equal, the controller completes calculation of the optimal amplification gain for the specific wavelength, and may calculate an optimal amplification gain for a next wavelength.

Referring back to FIG. 11, if, in 1120, the controller determines not to calculate the optimal amplification gain or, in 1130 has calculated the optimal amplification gain, the controller may drive the light source part for measuring bio-information in 1140, and may set the amplification gain of the VGA based on the optimal amplification gain calculated for each wavelength in 1150.

In 1160, the spectrometer part detects the optical signal of each wavelength returning from the object, converts the detected optical signal into an electric current signal and outputs the electric current signal. The spectrometer part converts the output current signal of each wavelength into a voltage signal, and amplifies and outputs the voltage signal in 1170. In 1180, the spectrometer part may convert the amplified and output analog signal into a digital signal, and may output the digital signal.

In 1190, the controller may restore the spectrum based on the digital signal output by the spectrometer part and may measure bio-information.

Figure 13A:
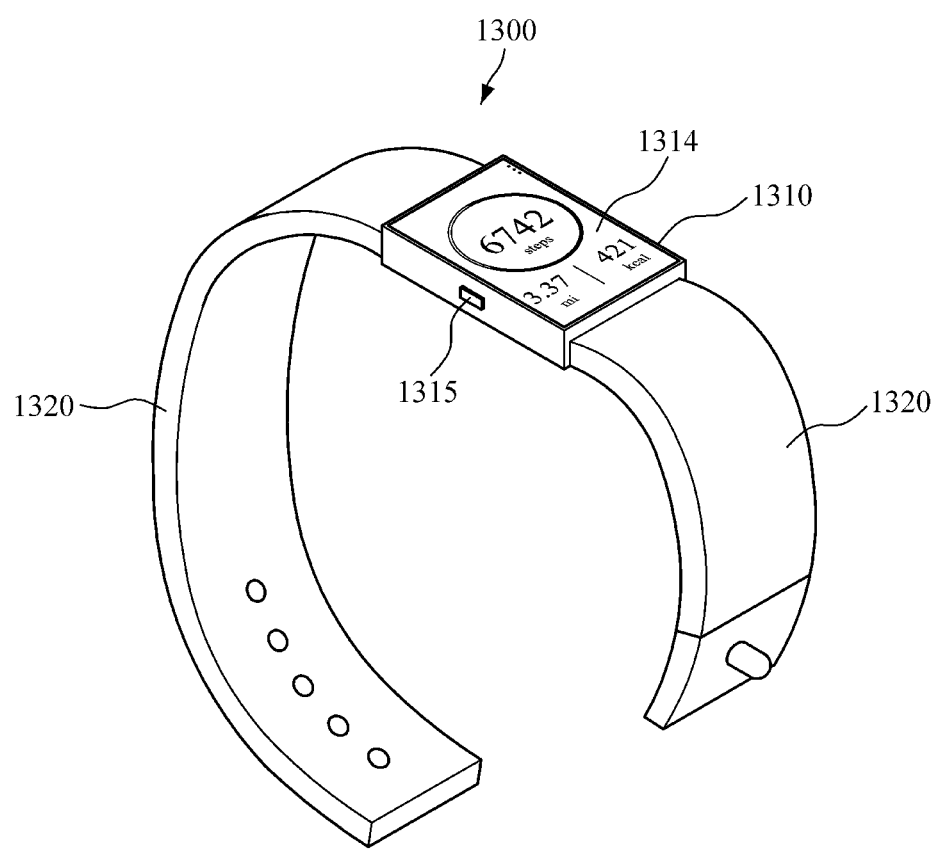
FIGS. 13A and 13B are diagrams illustrating a wearable device, according to exemplary embodiments.
Figure 13B:
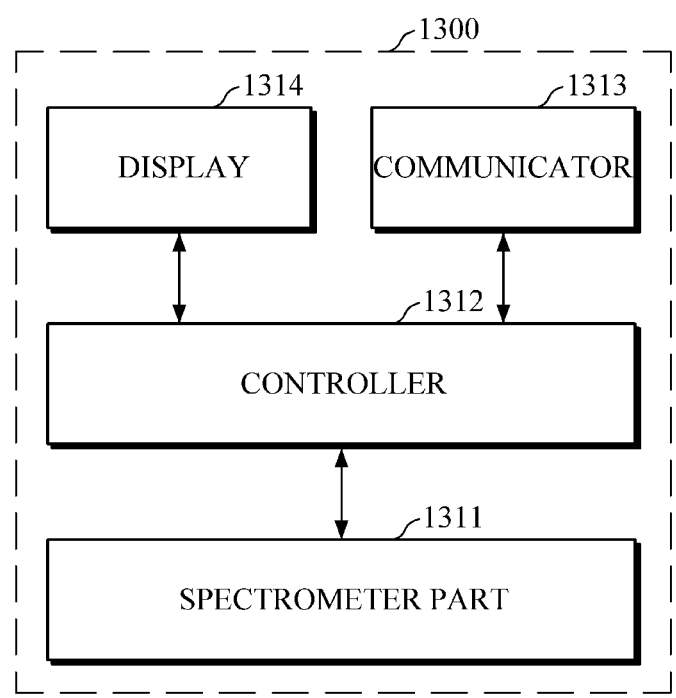

FIG. 13A is a diagram illustrating a wearable device, according to an exemplary embodiment. FIG. 13B is a block diagram illustrating a wearable device, according to an exemplary embodiment.

Referring to FIGS. 13A and 13B, the wearable device 1300 includes a main body 1310 and a strap 1320.

The main body 1310 may be worn with the strap 1320 around a user's wrist, and may include any of various members which are mounted in the main body 1310 or exposed to the outside thereof.

The strap 1320 may include a portions connected each side of the main body 1310 to be fastened to each other. The strap 1320 may be made of a flexible material to bend around a user's wrist so that the main body 1310 may be worn on a user's wrist.

Either one or both of the main body 1310 and the strap 1320 may include a battery which supplies power to the wearable device 1300.

The wearable device 1300 may further include a spectrometer part 1311 which is mounted at the main body 1310 to measure a spectrum reflected from a portion of a user's wrist. The spectrometer part 1311 may include features or functions described above with reference to FIG. 9. A light source of the spectrometer part 1311 may be provided at the bottom of the main body 1310 to be exposed to the wrist to emit light onto the wrist. Further, as illustrated in FIG. 2, the light source of the spectrometer part 1311 may be mounted at the bottom of the main body 1310 with a detector disposed at the center thereof and a light source array disposed on a circular frame.

The wearable device 1300 may further include a controller 1312 which is mounted in the main body 1310. The controller 1312 may receive a command from a user and may perform an operation according to the received command. For example, if the command received from user is a bio-information measuring command, the 1312 may control the spectrometer part 1311 accordingly. Further, once the spectrometer 1311 obtains an optical signal, reconstructs a spectrum based on the obtained optical signal, and outputs the reconstructed spectrum, the controller 1312 may measure bio-information based on the reconstructed spectrum. In this case, the controller 1312 controls each light source of the spectrometer part 1311 by time-dividing each of the light sources of the spectrometer part 1311, and at the time of driving each light source, the controller 1312 may set the amplification gain of the spectrometer 1311 based on an optimal amplification gain calculated for each wavelength, respectively.

Upon receiving a bio-information measuring command from the user, the controller 1312 may collect sensor information from various sensors, such as a tilt sensor or a contact pressure sensor mounted in the main body 1310, before measuring bio-information, and may determine whether to calculate an amplification gain based on the collected sensor information. For example, if tilt information included in the sensor information is different from previous tilt information by a value equal to or higher than a threshold value, or if a period during which a user has not worn the wearable device is equal to or longer than a predetermined period, the controller 1312 may determine that a portion to be examined is changed, and may determine to re-calculate an optimal amplification gain. Alternatively, if the controller 1312 determines that information of a contact pressure between the main body 1310 and the portion to be examined, which is included in the sensor information, is different from contact pressure information obtained during a previous measurement by a value equal to or higher than a threshold value, the controller 1312 may determine to re-calculate the optimal amplification gain.

Upon such a determination, if the controller 1312 determines to calculate the optimal amplification gain, or receives a request for calculating the optimal amplification gain from a user, the controller 1312 may calculate the optimal amplification gain for each wavelength by using the above-described method of calculating the optimal amplification gain.

Upon measuring bio-information, the controller 1312 may generate an alarm or warning information based on the measured bio-information and user information including, for example, age, gender, health state information, and the like.

The wearable device 1300 may further include a communicator 1313 which is mounted at the main body 1310. The communicator 1313 may be connected with an external device by using any of various communication techniques. The communicator 1313 may transmit bio-information to the external device so that the external device may perform any of various functions related to monitoring of a user's health state by using the bio-information. The external device may be an information processing device, such as a smartphone, a tablet PC, a desktop computer, a laptop computer, or the like, which has a relatively high computing performance.

In this case, the communication technique may include Bluetooth communication, Bluetooth Low Energy (BLE) communication, Near Field Communication (NFC), wireless local area network (WLAN) (WIFI) communication, Zigbee communication, Infrared Data Association (IrDA) communication, Wi-Fi Direct (WFD) communication, Ultra-Wideband (UWB) communication, Ant+ communication, WIFI communication, or mobile communication, but is not limited thereto.

The wearable device 1300 may further include a display 1314 which is mounted at the top of the main body 1310 and provides a processing result of the controller 1312 to a user. For example, the display 1314 may display bio-information measured by the controller 1312, or warning or alarm information. Alternatively, the display 1314 may display an interface to receive any of various commands from a user or guide a user. The display 1314 may be formed as a module enabling touch input, and may receive commands input by touch from a user, and may transmit the received commands to the controller 1312.

The wearable device 1300 may further include a manipulator 1315 which is mounted at the main body 1310. The manipulator 1315 may be exposed to the outside at one side of the main body 1310, may receive a control command input from a user, and may transmit the received control command to the controller 1312. The manipulator 1315 may have a function of turning on/off the wearable device 1300.

Exemplary embodiments described herein can be realized as a computer-readable code written on a computer-readable recording medium The computer-readable recording medium may be any type of non-transitory recording device in which data is stored in a computer-readable manner.

Examples of the computer-readable recording medium include, but are not limited to, a ROM, a RAM, a CD-ROM, a magnetic tape, a floppy disc, and an optical data storage. The computer-readable recording medium can be distributed over a plurality of computer systems connected to a network so that a computer-readable code is written thereto and executed therefrom in a decentralized manner. Functional programs, codes, and code segments needed for realizing the present invention can be easily deduced by one of ordinary skill in the art.

While exemplary embodiments have been described with reference to the figures, it will be understood by those of ordinary skill in the art that various changes in form and details may be made therein without departing from the spirit and scope as defined by the following claims.

What is claimed is:

1. A spectrometer, comprising:
a light source part configured to emit light of a plurality of wavelengths onto an object;
a detector configured to detect an optical signal of each of the plurality of wavelengths as reflected from the object;
a controller configured to set an amplification gain for each of the plurality of wavelengths according to at least one property of the object; and
an amplifier configured to amplify an output signal of the detector by using the amplification gain set by the controller,
wherein, for each specific wavelength of the plurality of wavelengths, the controller is further configured to calculate an optimal amplification gain based on a photoreaction property of the object for the specific wavelength.

2. The spectrometer of claim 1, wherein the light source part comprises a plurality of light sources comprising at least a first light source configured to output light of a first wavelength, and a second light source, configured to output light of a second wavelength, different from the first wavelength.

3. The spectrometer of claim 2, wherein the light source part is configured to output light from the first light source at a first time, and to output light from the second light source at a second time, different from the first time.

4. The spectrometer of claim 1, wherein, for each specific wavelength of the plurality of wavelengths:
when light of the specific wavelength is emitted by the light source part, the controller sets an amplification gain of the amplifier based on an optimal amplification gain of the specific wavelength.

5. The spectrometer of claim 4, wherein, for each specific wavelength, the controller calculates an optimal amplification gain, which does not saturate an output of the amplifier, for each of the specific wavelength by changing an amplification gain of the amplifier in a predetermined amplification gain section.

6. The spectrometer of claim 1, wherein the amplifier comprises:
a Trans-Impedance Amplifier (TIA) configured to convert a current signal output by the detector into a voltage signal; and
a Variable Gain Amplifier (VGA) configured to amplify the voltage signal by using the amplification gain set by the controller for each of the plurality of wavelengths.

7. The spectrometer of claim 1, further comprising a converter configured to convert an analog signal, which is amplified and output by the amplifier for each of the plurality of wavelengths, into a digital signal.

8. The spectrometer of claim 7, wherein the controller reconstructs a spectrum based on the digital signal output by the converter for each of the plurality of wavelengths.

9. The spectrometer of claim 8, wherein the controller obtains a first spectrum response based on the digital signal of the converter for each of the plurality of wavelengths, obtains a second spectrum response based on a value obtained by dividing the obtained first spectrum response by a value obtained by multiplying a light intensity and an optimal amplification gain for each of the plurality of wavelengths, and reconstructs a spectrum for measuring bio-information based on the obtained second spectrum response.

10. A method of obtaining a spectrum by a spectrometer, the method comprising:
emitting, from a light source part, light of a plurality of wavelengths onto an object;
setting, by a controller, an amplification gain for each of the plurality of wavelengths according to at least one property of the object;
detecting, by a detector, an optical signal of each of the plurality of wavelengths as reflected from the object;
amplifying, by an amplifier, an output signal of the detector by using the amplification gain set by the controller; and
calculating, by the controller, for each specific wavelength of the plurality of wavelengths an optimal amplification gain based on a photoreaction property of the object for the specific wavelength.

11. The method of claim 10, further comprising converting, by a converter, an analog signal, which is amplified and output by the amplifier for each of the plurality of wavelengths, into a digital signal.

12. The method of claim 11, further comprising the controller reconstructing a spectrum based on the digital signal for each of the plurality of wavelengths.

13. The method of claim 10, further comprising: for each specific wavelength of the plurality of wavelengths:
when light of the specific wavelength is emitted in the emitting of the light onto the object, setting an amplification gain of the amplifier based on an optimal amplification gain of the specific wavelength.

14. The method of claim 13, wherein, for each specific wavelength, the calculating of the optimal amplification gain comprises:
driving the light source part to emit light of the specific wavelength with a predetermined light intensity onto the object;
while light of the specific wavelength is emitted onto the object, changing an amplification gain of the amplifier in a predetermined amplification gain section; and from among the changed amplification gains, selecting a maximum amplification gain, which does not saturate an output of the amplifier, to be an optimal amplification gain for the specific wavelength.

15. The method of claim 14, wherein the selecting the optimal amplification gain comprises, in response to the selected optimal amplification gain being equal to a maximum amplification gain in the amplification gain section, adjusting a light intensity of the specific wavelength, and repeating the emitting of the light of the specific wavelength and the changing the amplification gain.

\* \* \* \* \*